US008568293B1

(12) United States Patent
Rao

(10) Patent No.: US 8,568,293 B1

(45) Date of Patent: Oct. 29, 2013

(54) SURGICAL SPAY AND NEUTER ASSIST PLATFORM SYSTEM

(76) Inventor: Subhakar Patthi Rao, Thousand Oaks, CA (US)

(*) Notice: Subject to any disclaimer, the term of this patent is extended or adjusted under 35 U.S.C. 154(b) by 197 days.

(21) Appl. No.: 13/229,564

(22) Filed: Sep. 9, 2011

Related U.S. Application Data

(60) Provisional application No. 61/385,827, filed on Sep. 23, 2010.

(51) Int. Cl.
*A61B 17/3205* (2006.01)

(52) U.S. Cl.
USPC .............................................................. 600/37

(58) Field of Classification Search
USPC .................... 600/37, 201–246; 606/139–159, 606/232–233
See application file for complete search history.

(56) References Cited

U.S. PATENT DOCUMENTS

| | | | | |
|---|---|---|---|---|
| 5,779,629 | A * | 7/1998 | Hohlen | 600/233 |
| 5,813,978 | A * | 9/1998 | Jako | 600/201 |
| 7,722,639 | B2 | 5/2010 | Dowling | |
| 2006/0079932 | A1 | 4/2006 | Dowling | |

* cited by examiner

*Primary Examiner* — Charles A Marmor, II
*Assistant Examiner* — Catherine E Burk

(57) ABSTRACT

In accordance with one embodiment a surgical device consisting of a rigid frame with a spindle straddling the lateral members and coupled with a ratcheting traction unit for the purpose of anchoring an organ and, to apply controlled incremental traction to the tissues connecting the organ to the body enabling exposure of a working length of the tissue and its associated structures for the application of ligatures etc.

2 Claims, 9 Drawing Sheets

SURGICAL SPAY AND NEUTER ASSIST PLATFORM SYSTEM

CROSS REFERENCE TO RELATED APPLICATIONS

Provisional U.S. Application No. 61/385,827, filed on Sep. 23, 2010 by Subhakar Patthi Rao for a "Surgical Spay and Neuter Assist Platform System" ('SNAP' system).

BACKGROUND

Prior Art (1) Patent # US 2006/0079932 A1 issued to Brian T. Dowling on Apr. 13, 2006

(2) The 'Hauptman OHE Retractor' available from Jorgenson Laboratories of Loveland Colo.

FEDERALLY SPONSORED RESEARCH

None

Surgical neutering (Ovario-hysterectomy or removal of the female reproductive organs commonly referred to as 'Spaying' and, Orchiectomy is the removal of the testes in the male is usually referred to as 'Castration') is one of the most routinely performed elective procedures carried out by veterinarians. It demands a working knowledge of regional anatomy, skill and, manual dexterity. In the case of 'Spaying' sometimes an 'additional' pair of hands comes into play to complete the procedure.

After gaining access to the abdomen of the female dog or cat, the uterine horn is identified, isolated, exteriorized and followed cranially to locate the ovary. Once this is done the ovary is held by the 'Proper' ligament (the ligament that attaches the ovary to the uterus) and adequate traction is applied to identify the 'suspensory' or ovarian ligament (a strong fibrous band that is attached to the ovary at the distal end and arises as a fan shaped structure from the vertebral end of the last two ribs) by digital palpation as a taut band arising from the an area near pole of the ipsilateral kidney. Holding and maintaining traction on the proper ligament by the power hand, the index finger of the free hand is slid along the cranial border of the suspensory ligament (closer to the kidney) and is either stretched or torn to facilitate exteriorizing the ovary.

At this stage a 'fenestration' or a window is made in the broad ligament (the structure that comprises of a peritoneal fold that suspends the uterus) caudal to the ovary and one or two crushing type of forceps (depending upon the choice of the surgeon) are placed across the ovarian 'Pedicle' (comprising of the tortuous ovarian artery and vein; the suspensory ligament and its vasculature) and one across the proper ligament. Once removed, the most proximal clamp serves to form a groove for the placement of a circumferential ligature which is applied in a fashion that is comfortable to the surgeon. The middle clamp assists to hold the pedicle for ligation. Depending upon the skill of the surgeon, size of the pedicle and the amount of fat surrounding it a second ligature may be applied after releasing (and 'flashing') the middle forceps. The suspensory ligament is held as close to the ovary as possible by a smaller forceps and the pedicle is transected distal to this forceps. The stump is checked for any bleeding and is released back into the abdominal cavity. The contralateral ovary is removed in the same way. Removal of the uterus is done in a routine way.

The preceding paragraph illustrates the steps needed to complete the procedure (in this instance removal of the ovaries) after the body wall is opened the ovaries need to be exteriorized and the pedicle visible and accessible for the application ligatures. There has to be adequate traction applied to the ovarian pedicle to keep the ovary in an exteriorized position.

While maintaining traction, the index finger of the free hand is used to feel for the taut ovarian ligament and with controlled traction from the said finger the said ligament is 'tweaked' until it tears or stretched for adequate pedicle exposure. Since the application of the ligature requires two hands, the step to hold the traction on the ovarian pedicle lies in the improvisation of the surgeon using the back or the edge of the palm to anchor the clamps or seek the assistance from an extra pair of hands. One method to secure and stabilize the ovarian pedicle (for a solo surgeon) is to apply a crushing clamp (or two clamps placed opposite to each other across the opened body wall) proximal to the intended placement of the ligature, apply the ligature and release the clamp (or clamps). Since the groove or tract made by the clamp is left behind in the body, there is a chance that the integrity of the vascular walls of the pedicle might be compromised leading to bleeding and subsequent complications.

At present there are two alternatives that offer relief for the solo practitioner:

(a) The 'Hauptman OHE Retractor' (available in three sizes from Jorgenson Laboratories of Loveland Colo.) lets the veterinary surgeon clamp the proper ligament (using existing clamps like the Carmalt etc) after stretching or tearing the suspensory ligament make a fenestration in the broad ligament to pass the lower arm of the retractor and use the two prongs to secure the clamp. Steady traction is applied on the pronged arm away from the bottom arm to stretch, stabilize and pull the ovarian pedicle into view and then proceed to ligate the same. The taut ovarian pedicle over the straight bottom arm of the device tends to act as a 'fulcrum' and as such the set up could have a tendency to lift up.

(b) The 'Dowling Retractor' invented by Brian T. Dowling of Elma Wash., (patent # US 20060079932A1, date: Apr. 13, 2006) is a much simpler rendition. Before clamping the proper ligament the surgeon has to secure the ligament using his fingers (and a piece of gauze for added traction) to wiggle and exteriorize the ovary, make a fenestration in the broad ligament, pass the fixed lower curved arm of the retractor through the opening and apply enough traction to exteriorize the ovarian ligament and then place the clamp across the proper ligament. Depending upon the amount of traction that is applied to the ovarian ligament, the tip of the lower curved arm (if it lacks adequate support from the body wall) could have a tendency to tip over as the curved arm could act as a fulcrum. The said retractor is available in two lower arm sizes.

The shortcomings of the aforementioned retractors is based on the laws of physics, specifically that of Class I Levers and the fulcrum which is placed farther away from the load (here the attachment of the ovarian ligament and its associated structures) than it is to the point of force (the forceps clamped across the proper ligament) and as such a significantly higher tendency for the device to tip over.

ADVANTAGES

The described embodiment offers a more stable and elegant solution to expose the ovarian ligament with a more controlled traction as the device takes advantage of the fulcrum in Class I Levers. When the load increases (tension from the ovarian ligament) so does the stability of the device and prevents any tipping over. This device can accommodate anatomical variations as reproductive anatomical parts come in different sizes and lengths. There is no need to break the ovarian ligament for a working exposure of the ligament and the veterinarian has both the hands free to ligate the pedicle in a more comfortable manner. The procedural time is shortened since this device eliminates the step of breaking the ovarian ligament and there is no 'fumbling' of the instrumentation to complete the application of the ligatures. This device is to augment the standard set of instruments that are routinely used in spay and neuter procedures.

In a neutering procedure the 'cord' is clamped and anchored between the two prongs and adequate traction applied to stretch the same. A second clamp is temporarily applied across the cord to 'crush' the cremaster muscle and provide a track for the application of the ligature.

SUMMARY

The 'SNAP' System addresses the need to a more secure, controlled, and confident method of exposing and anchoring reproductive tissues when performing one of the most common surgical procedures (spaying and neutering) in a veterinary hospital.

In accordance with the described embodiment (the 'SNAP' system) consists of a rigid frame and a spindle straddling the lateral members. The traction unit resembles a 'three-tined pitchfork' or a 'trident' shape with a flat stump for a handle. The stump is attached to a set of prongs cranially and the central tine is shaped in the form of a flat ratcheting bar that slides into a channel located in the ratcheting housing that is located on the rear cross member. The rear opening of the channel has a partial height beveled end plate attached at a predetermined height to act as a rigid pawl to control the movement of the ratcheting bar. The traction system has a pair of guide rods on either side of the ratcheting bar that slide in and out the corresponding open sleeves found on the traction housing. This set up will help align the unit and prevent the same from racking during operation. To impart traction, the thumb support on the traction unit and the finger grip on the traction unit housing are squeezed together. To release the ratcheting bar, downward digital pressure is applied to the caudal tip of the ratcheting bar to disengage the ratcheting teeth and slide the bar out cranially.

In accordance with another simpler rendition of the device the mechanical traction system is eliminated and instead the caudal portion of the rigid lateral members of the main frame sports a plurality of caudally raked congruent notches on the dorsal surface.

The proper ligament is cross-clamped with the power hand using user supplied forceps; the thumb and fingers of the free hand are placed on either side of the central annular concavity of the spindle to stabilize the frame and to apply downward pressure. The tip of the forceps is maneuvered into the first notch on the far side and this is used as a pivot to maneuver the body of the forceps into the corresponding first notch on the near side. This operation of 'walking' and alternately pivoting the tip and the body of the forceps is progressively advanced till a working length of the ovarian ligament is exposed.

DRAWINGS

REFERENCE NUMERALS

101 is the cranial cross member of the rigid frame.

102L & 102R are the two lateral members of the rigid frame.

103 is the spindle seen in an operational position.

104L & 104R the set of prongs that support the user supplied forceps.

105 the body of the traction unit with the dorsal thumb support.

105A the thumb support on the body of traction unit.

106L & 106R are the lateral guide rods of the traction unit.

107 is the finger support that is on the top of the traction unit housing.

108 is the ratcheting bar of the traction unit.

109 is the caudal cross member of the rigid frame.

110 is the rigid platform that rests on the prepped and draped abdomen of the pet.

111L & 111R are the two congruent cranially raked notches that receive the spindle

112 is the sliding traction unit.

113 is the housing for the sliding traction unit.

115L & 115R are the tubular channels for the movement of the lateral guide rods.

116L & 116R are the openings of the tubular channels.

117 is the beveled fixed pawl to stop the cranial movement of the ratcheting bar.

118 is the cranial opening of the channel that receives the ratcheting bar.

119A & 119B are the ends of the spindle that will rest in the notches of the rigid frame.

120A & 120B are the collars that prevent the lateral movement of the spindle while seated in the notches of the rigid frame.

121A & 121B are rings that guide the connecting tissues to the center of the spindle.

122 is the central annular concavity that channels the connecting tissues.

123 is the rigid frame of the second embodiment.

124L & 124R are a set of caudally raked congruent notches to trap the user supplied forceps.

DETAILED DESCRIPTION

Figure 1:
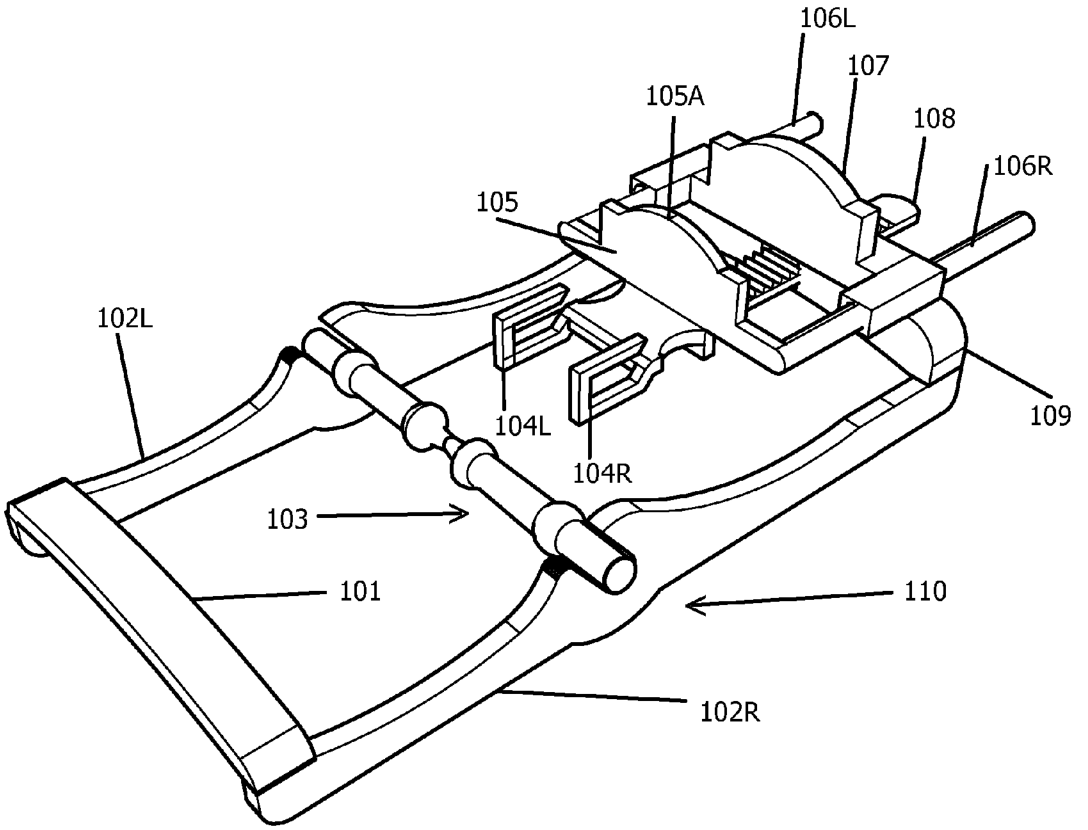
FIG. 1 is the one of the embodiments of the 'SNAP' system.

FIG. 1 is a perspective view of the device showing the embodiment in an assembled state that is ready for use. The two prongs 104R and 104L helps anchor the forceps that is clamped across the proper ligament. The squeezing together of the thumb support 105A and the finger support 107 helps the application of necessary traction to expose a working length of the ovarian ligament and its associated structures. Other parts are the spindle 103, the main rigid frame 110.

Figure 2:
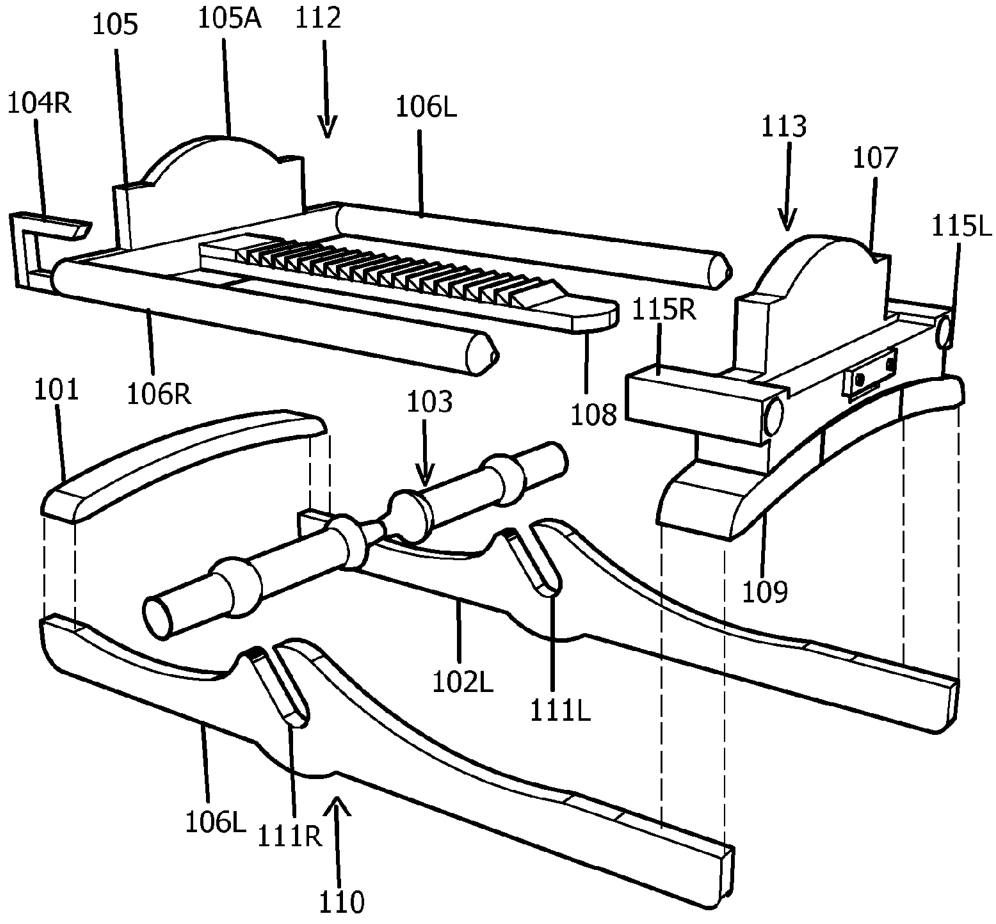
FIG. 2 is an exploded view showing the parts of the 'SNAP" system.

FIG. 2 is an exploded view of the embodiment. The cross members 101 and 109 to be permanently attached to the lateral members 102R and 102L of the rigid frame 110. The pair of cranially rake notches 111R and 111L located on the dorsal surface of the lateral members receives the ends of the spindle 103 during operation. The raised fixed vertical member 105A behind the prongs serves as a support for the thumb and the upright raised member 107 which is located at the entrance of the traction housing 113 serves as resting place for the fingers of the surgeon during the act of applying traction to the connecting ovarian structures. The ratcheting bar 108 of the sliding part of the traction unit helps maintain traction on the ovarian structures during operation and can be disengaged by the surgeon as needed.

Figure 3:
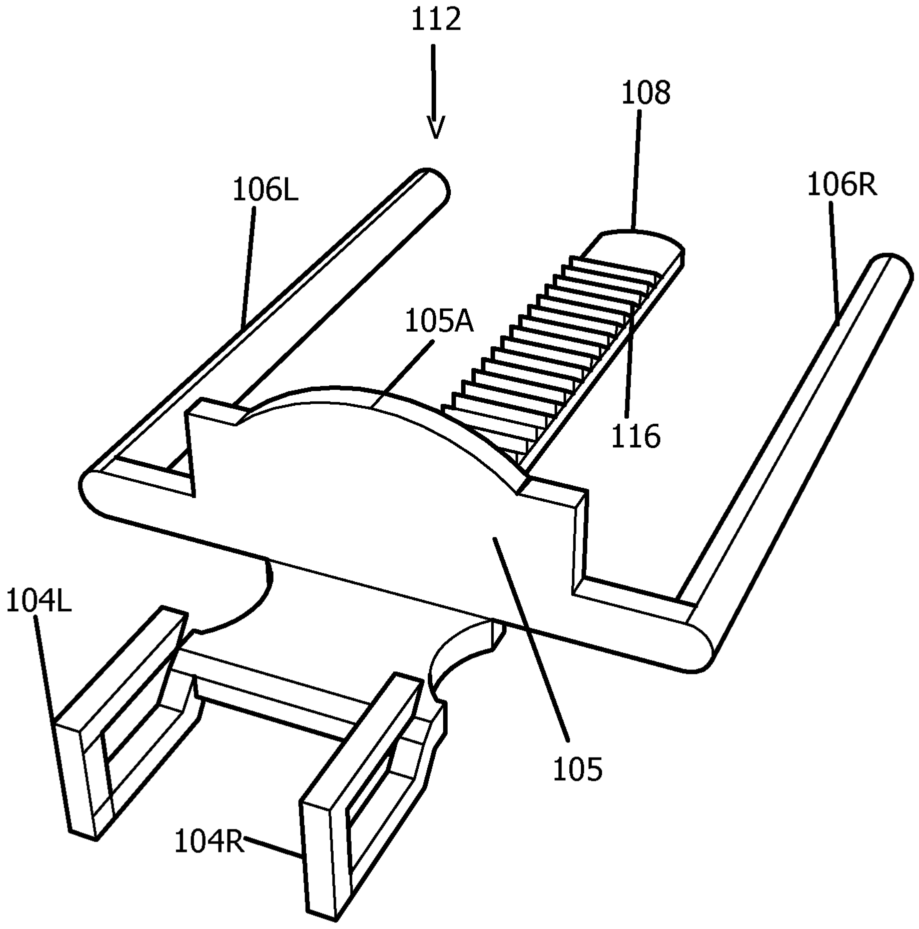
FIG. 3 is the sliding components of the traction unit.

FIG. 3 shows the sliding traction unit 112, the body 105, the thumb support 105A and, the centrally located flat ratcheting bar 108 shows a set of cranially raked elongate teeth 116 on the dorsal surface. The two guide rods 106R and 106L located laterally prevent the sliding unit from racking during operation. The two prongs 106R and 106L in front of the body 105.

Figure 4:
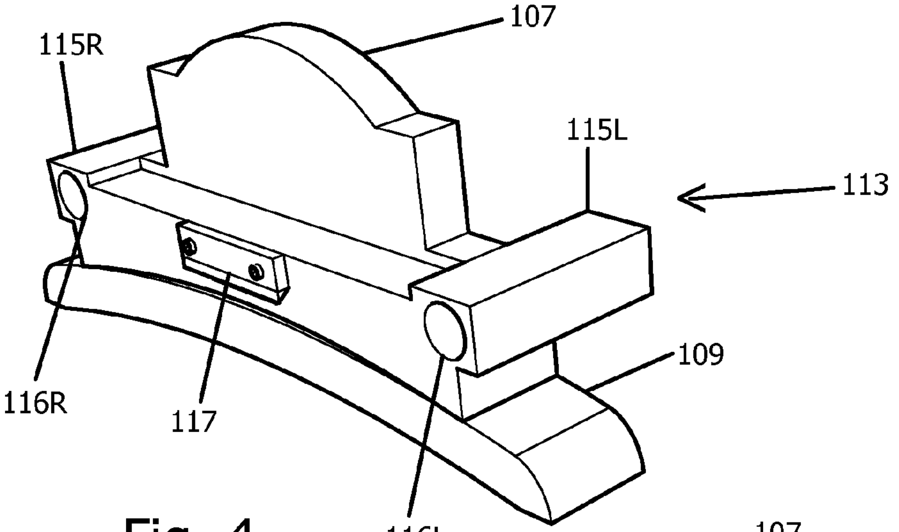
FIG. 4 is the caudal view of the traction unit housing

FIG. 4 shows the caudal view of the traction unit housing located above the caudal cross member 109. The lateral channels 115R and 115L show the two hollow tubes 116R and 116L that receives the two guide rods during operation. The fixed beveled rigid pawl 117 located at a predetermined height above the caudal opening of the central channel serves to lock the sliding ratcheting bar as needed.

Figure 5:
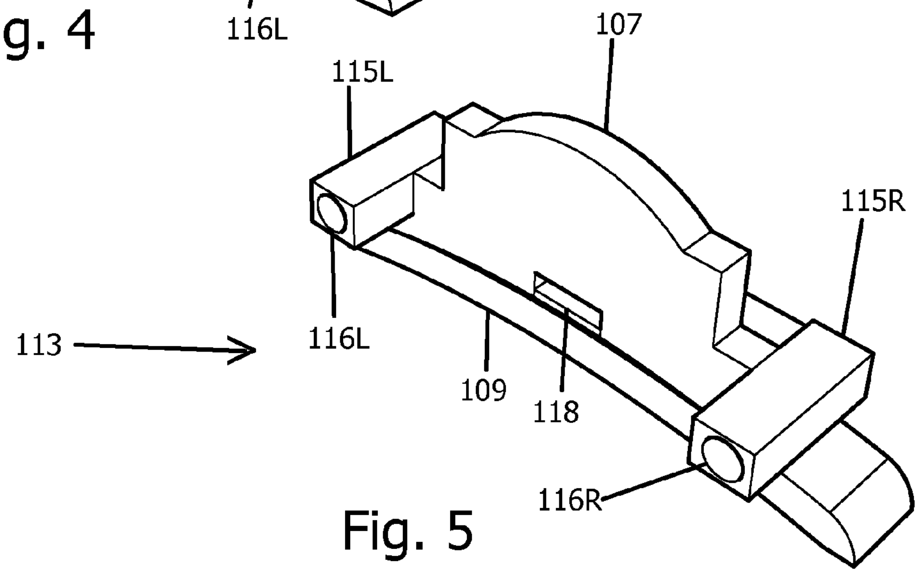
FIG. 5 is the cranial view of the traction unit housing

FIG. 5 shows the cranial view of the traction unit housing located above the caudal cross member 109. The cranial opening of the central channel 118 receives the flat ratcheting bar of the sliding traction unit. The lateral channels 115R and 115L show the two hollow tubes 116R and 116L that receives the two guide rods during operation.

Figure 6:
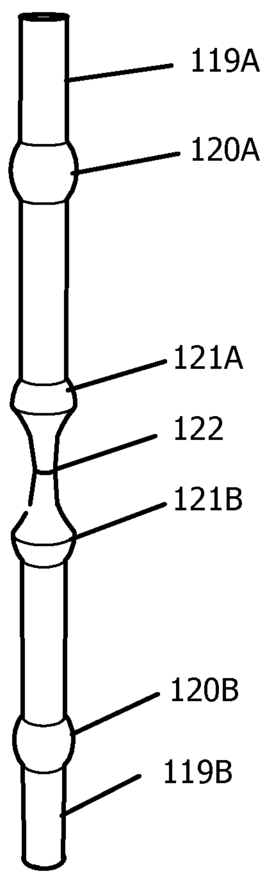
FIG. 6 is the rigid spindle.

FIG. 6 shows the spindle 103. The two collars 120A and 120B prevent the spindle from sliding out of the dorsal notches 111R and 111L located on the lateral members 102R and 102L. The central annular sulcus 122 is bounded by a set of annular rings 121A and 121B that help guide the ovarian structures to stay confined within the concavity of the annular sulcus 122.

Figure 7:
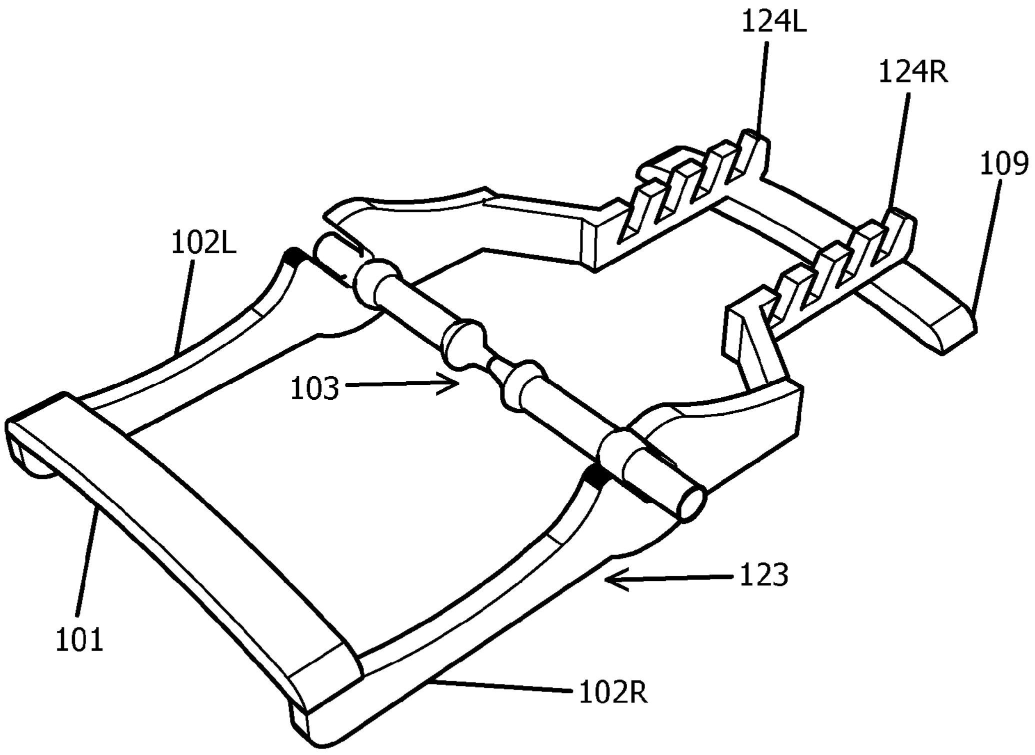
FIG. 7 is another embodiment of the 'SNAP' system.

FIG. 7 shows a simpler rendition of the surgical device without a built-in traction unit. The caudal portion of the modified lateral members of the rigid frame 123 have a set of dorsally placed caudally raked congruent notches in areas 124R and 124L. These notches help in pivoting the tip and the body of the forceps to advance caudally and incrementally expose the ovarian ligament and its associated structures. Other parts are the spindle 103, the modified main frame 123 and the rear cross member 109.

Figure 8:
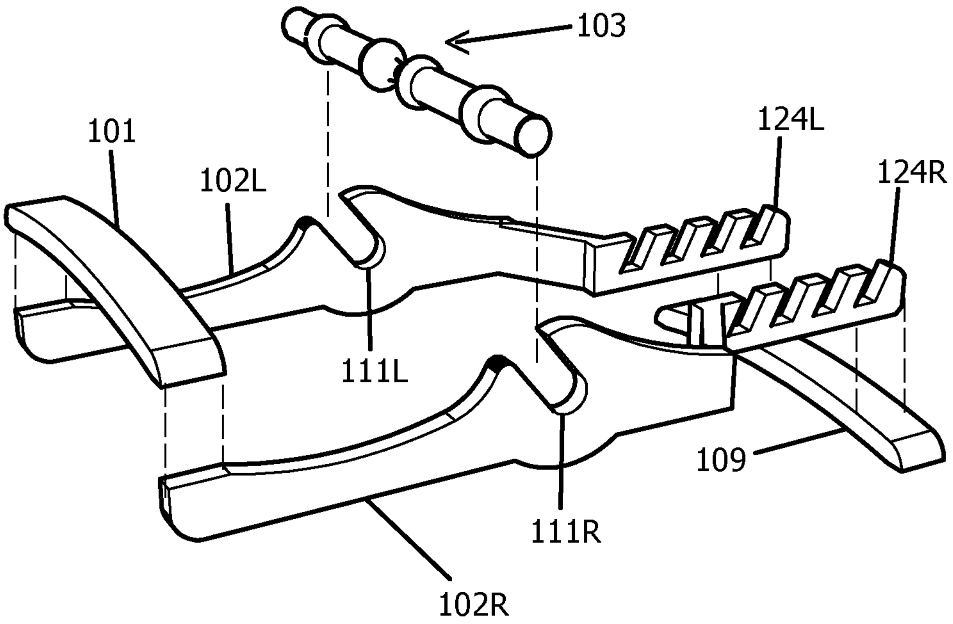
FIG. 8 is an exploded view of the second embodiment.

FIG. 8 shows an exploded view of the simpler version of the device. Cranial cross member 101, caudal cross member 109, lateral members 102R and 102L to be permanently fused in the predetermined configuration. Dorsal notches 111R and 111L receive the spindle 103.

Figure 9:
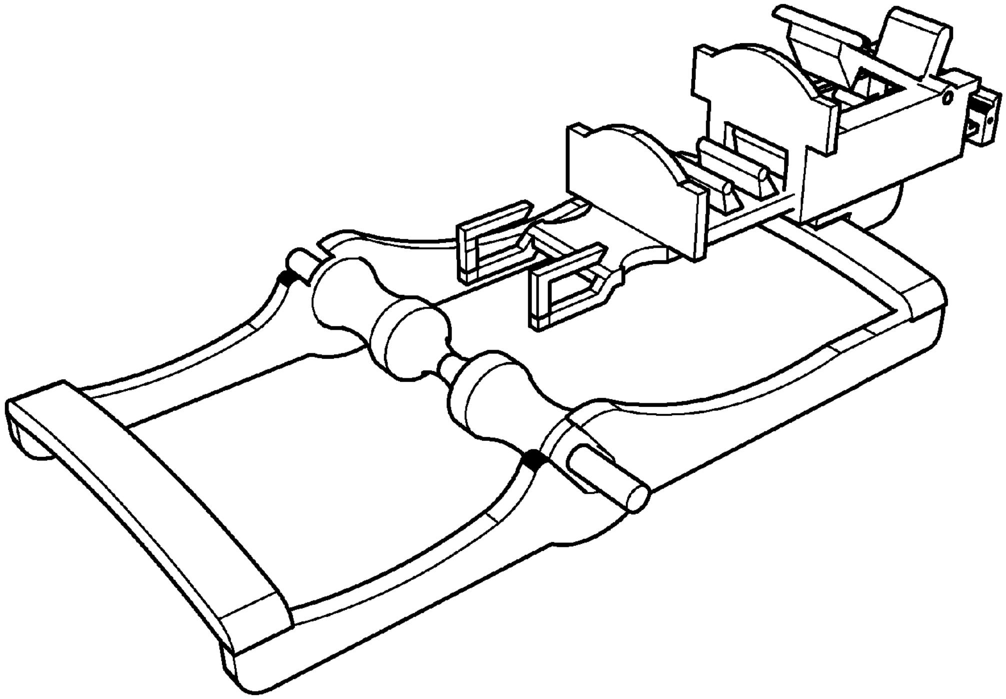
FIG. 9 is a variation of the 'SNAP' system.

FIG. 9 shows the embodiment with a variation of the traction unit with an articulating pawl and a modified spindle.

Figure 10:
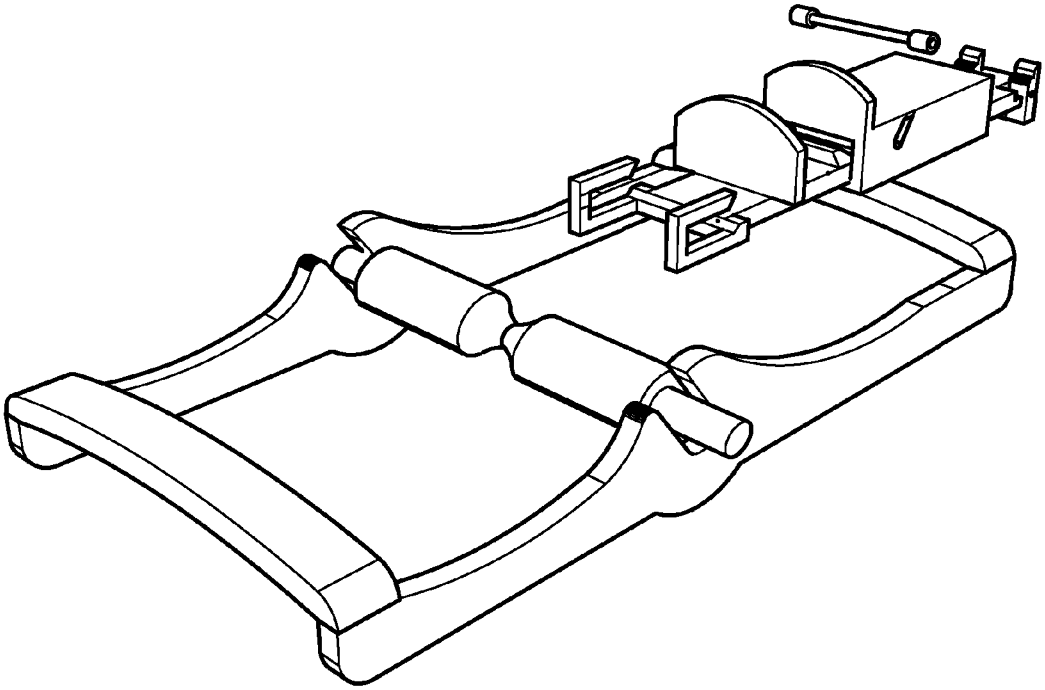
FIG. 10 is yet another variation of the 'SNAP' system.

FIG. 10 shows yet another embodiment with a variation of the traction unit showing an unassembled floating roller pin instead of a pawl and another variation of the spindle.

MATERIALS, RAMIFICATIONS AND CONCLUSIONS

The embodiment to be made with a metal that is light weight, can withstand thermal stress that typical surgical instruments undergo during the sterilization process, be resistant to body fluids and chemicals in the cleaning solutions, be resistant to corrosion or oxidative damage, be adequately hard to withstand routine surgical handling and occasional mishandling, retain surface integrity for ease of use and cleaning etc. Options would include 316L or 904L type of surgical grade stainless steel or, production costs permitting Titanium could also be considered.

The top contact surface of the raked dentils on the ratcheting bar and the lower beveled edge of the fixed pawl could be laminated with tungsten carbide inserts to extend the longevity of the device.

The anterior face of the thumb support on the ratcheting body and the posterior face of the finger support on the ratcheting stop housing unit could have a milled cross-hatched or reticulated surface to increase frictional grip during the traction process.

The lateral members of the frame, the sliding traction unit, the traction housing of the embodiment to be 'bead' blasted (glass bead #10 size with a mesh of 100/170) or other similar process to give it a soft satin luster thereby reducing any reflections from the lights in the operatory and marginally increase haptic properties. For purely aesthetic reasons, the two cross members to have a polished satin finish.

In accordance with another variation of the device a larger sliding ratcheting platform travels in a open channel located in the ratcheting pawl housing and the movement of the ratcheting platform is controlled by an articulating pawl that is secured atop the housing. The sliding platform has an articulating stop at the caudal end that prevents the platform from sliding completely out of the housing during a surgical procedure. The pawl can be engaged or disengaged depending upon the different stages of the surgical procedure. The pawl housing unit is attached to the rear cross member of the metal frame.

In accordance with another variation of the articulating pawl would be to replace the articulating pawl with a roller pin with capped ends that travels in caudally raked embrasures located in the side walls of the housing. The pin mates with the raked teeth on the sliding ratcheting platform and it moves up in the opening when the platform is pushed caudally into the housing and drops in front of the teeth thereby locking the platform.

In accordance with yet another embodiment of the device provides the necessary traction via a horizontally placed gear that is attached to a lever at the top. The gear meshes with a ratcheting bar that bears dentils on the lateral side facing the gear and, the bar bears a set of prongs at the cranial end. The movement of the gear is controlled by an articulating spring loaded pawl with a thumb grip to facilitate the engagement or disengagement of the pawl. To impart the necessary traction to the ovarian ligament the lever is moved in a radial direction till the ligament is in a position to be ligated With all the variations shown, the reader will see at least one embodiment of the surgical device to be more effective and easy to operate. These embodiments are simple in design, light-weight and economical to manufacture. The specificities of the description should not be construed as limitations of the scope of the embodiments but rather as an exemplification of several variations. In keeping with the principle of the class-1 levers, the embodiment can be designed to adapt to other organs that need to be secured when exteriorized outside the body.

Operation

This description follows after the anesthetized patient has undergone a celiotomy and the uterine horn with the connected ovarian structures (the side nearest to the surgeon) is exteriorized. The proper ligament is identified and cross-clamped with a forceps. The forceps is held above the surface of the abdomen and the broad ligament is identified and a small (size adequate for the passage of the spindle) fenestration is made just below the proximal limit of the ovary. The forceps is now transferred to the free hand and the power hand secures the uterine horn. At this juncture the forceps (still cross clamped to the proper ligament) is let to passively drape on the near side of the body. The uterine horn is followed caudally towards the bifurcation and the far side uterine horn is exteriorized, (in younger patients the body wall incision may have to be extended caudally to reach the uterine bifurcation) cross clamped with a second forceps and a second fenestration is made in the broad ligament below the ovary.

Both the forceps (that are still securely clamped to the proper ligaments) are held up vertically with one hand and passed thru the rigid frame of the device (the prongs of the sliding rack is set at full extension) which is placed on the draped surface of the abdomen centering the celiotomy opening. The spindle is now passed thru the two fenestrations and the ends are placed in the two notches in the lateral members of the main frame. The forceps and the uterine horn that is away from the operator are draped over the farther side of the rigid frame. The forceps that is near to the operator is held by the power hand, the ovarian ligament and its associated structures are guided over the central annular concavity of the spindle and the forceps is secured behind the two prongs of the sliding rack. The rigid frame of the device can be repositioned to ensure that the ovarian ligament below the spindle is in a near vertical position.

If the forceps cannot be comfortably placed in the prongs, a little downward pressure on the spindle by the free hand should achieve the desired objective. Now the thumb grip on the sliding traction component and the finger support on the traction unit housing are squeezed together using the fingers of the power hand alone or with both the hands. This exposes a working length of the ovarian ligament and the associated structures. The structures are ligated based the surgeon's choice of material and method. A smaller forceps is used to clamp the ovarian ligament that is distal to the placement of the ligature and below the proximal end of the ovary. The pedicle comprising of the vasculature, other soft tissue and the ovarian ligament is transected distal to the small forceps. The cut end of the pedicle is checked for any hemorrhage and released into the abdominal cavity. The forceps is removed from the prongs of the sliding ratcheting platform and let to drape on the side of the body wall nearest to the operator.

The caudal tip of the ratcheting bar is digitally depressed and pulled out to the original extended position and digital pressure released to engage in the rigid pawl. The same steps are now followed for the second ovary and uterine horn. The spindle is now removed from its position and set aside. Both the forceps (that are still cross clamped to the respective proper ligaments) are held up and checked to ensure that no tissue or small organs are trapped in the bifurcation. The two broad ligaments attached to the uterine horns are manually separated making sure any small vessels are properly ligated. The uterine horns are straightened cranially and the spindle is now placed on top of the horns and dropped in the notches. The frame is slid back caudally to a position where the seated spindle is just above the caudal commisure of the abdominal incision. One of the forceps that is cross-clamped on the proper ligament is released and the same forceps is reapplied across both the exposed uterine horns at a level that is in line with the two prongs of the traction unit. The forceps with clamped uterine horns is set in the prongs. Moderate traction is applied to the uterine structures which are ligated based on the operator's choice of method and material. The second forceps that is still attached to the other proper ligament is released and applied across the uterine structures that are between the applied ligatures and the prongs of the sliding bar. The uterine structures are transected just between the applied forceps and the prongs. The stumps are checked for any hemorrhage and released back into the abdominal cavity. The embodiment is removed and set aside. The celiotomy incision is closed based on the choice of the surgeon.

I claim:

1. A surgical device to be used with a pair of operator supplied forceps to anchor an organ outside a body comprising:

(a) a plurality of elongate members forming a rigid frame adapted to surround a surgical opening, (b) a set of lateral members of said rigid frame, each lateral member having a dorsal region, a ventral region, a cranial portion, a caudal portion, and a mid-section in between, the said mid-sections have a pair of congruent notches on the dorsal region, (c) a set of cross members of the said rigid frame, each cross member having terminal portions and a mid-section in between, said cranial portions of said lateral members are fixedly attached to the said terminal portions of one of the said cross member forming a cranial cross member, and said caudal portions of the said lateral members is fixedly attached to the said terminal portions of another said cross member forming a caudal cross member, and said cross members are contoured to adapt to the natural curvature of said body, (d) a rigid spindle straddles the congruent notches of said lateral members during an anchoring and a traction procedure, wherein said rigid spindle has a set of limiting collars near the ends to prevent it from sliding out of said congruent notches of said lateral members and, said rigid spindle has a central region in between said limiting collars, said central region of said rigid spindle has a set of rings bounding a central annular concavity to guide and contain a connecting tissue during said traction, and (e) a traction unit is fixedly attached to the mid-section of said caudal cross member, said traction unit consists of a slidable component and a fixed housing.

2. The surgical device of claim 1 wherein said slidable component of said traction unit comprises of a body, said body of said slidable component has a dorsal area, a ventral area, an anterior surface and, a posterior surface, there is a thumb support on said dorsal area of said body of said slidable component, said body of said slidable component also has a set of prongs on said anterior surface, said posterior surface of said body of said slidable component has a ratcheting bar with a free end, said ratcheting bar has a dorsal surface and a ventral surface, a plurality of cranially raked congruent dentil are disposed on said dorsal surface of said ratcheting bar, said posterior surface of said body of said slidable component also has a set of guide rods on either side of the said ratcheting bar, said fixed housing of said traction unit has a cranial end, a caudal end, a dorsal area and a ventral area, a set of congruent openings connect said cranial end and said caudal end, and said ratcheting bar and said set of guide rods slide in and out of said fixed housing thru said set of congruent openings, said fixed housing has a finger support on the dorsal area, the caudal end of the said congruent opening for said ratcheting bar has a process to lock the movement of said ratcheting bar as needed, depressing the free end of said ratcheting bar releases the capture of said dentil from said process found on said caudal end of said congruent opening.

* * * * *